(12) United States Patent
Tann et al.

(10) Patent No.: US 9,433,208 B2
(45) Date of Patent: *Sep. 6, 2016

(54) CROP OIL CONCENTRATE ADJUVANTS CONTAINING AMINE SURFACTANTS

(71) Applicant: Huntsman Petrochemical LLC, The Woodlands, TX (US)

(72) Inventors: R. Scott Tann, Sugar Land, TX (US); Howard M. Stridde, George West, TX (US); Curtis M. Elsik, The Woodlands, TX (US)

(73) Assignee: HUNTSMAN PETROCHEMICAL LLC, The Woodlands, TX (US)

( * ) Notice: Subject to any disclaimer, the term of this patent is extended or adjusted under 35 U.S.C. 154(b) by 79 days.

This patent is subject to a terminal disclaimer.

(21) Appl. No.: 14/278,058

(22) Filed: May 15, 2014

(65) Prior Publication Data

US 2014/0249032 A1    Sep. 4, 2014

Related U.S. Application Data (62) Division of application No. 10/591,266, filed as application No. PCT/US2005/007057 on Mar. 3, 2005, now Pat. No. 8,765,637.

(60) Provisional application No. 60/549,825, filed on Mar. 3, 2004.

(51) Int. Cl.
| | |
|---|---|
| *A01N 25/00* | (2006.01) |
| *A01N 25/30* | (2006.01) |
| *A01N 25/02* | (2006.01) |
| *A01N 25/04* | (2006.01) |

(52) U.S. Cl.
CPC .............. *A01N 25/30* (2013.01); *A01N 25/02* (2013.01); *A01N 25/04* (2013.01)

(58) Field of Classification Search
None
See application file for complete search history.

(56) References Cited

U.S. PATENT DOCUMENTS

| | | | |
|---|---|---|---|
| 6,156,705 | A | 12/2000 | Mueninghoff |
| 6,464,996 | B1 | 10/2002 | Kowalik et al. |
| 6,541,424 | B2 | 4/2003 | Roberts et al. |
| 6,617,303 | B1 | 9/2003 | Smith et al. |
| 6,803,345 | B2 | 10/2004 | Herold et al. |
| 2003/0096726 | A1 | 5/2003 | Smith et al. |
| 2003/0148889 | A1 | 8/2003 | Herold et al. |
| 2004/0142823 | A1 | 7/2004 | Elsik et al. |

*Primary Examiner* — Alton Pryor
(74) *Attorney, Agent, or Firm* — Huntsman International LLC (57) ABSTRACT

In agricultural practice it is known to use emulsifiable oils (commonly referred to a Crop Oil Concentrates, COC) as bioefficacy enhancers for pesticides, especially herbicides. Cationic surfactants are widely known to be particularly effective bio-active enhancers for herbicides, especially for glyphosate-type herbicides. The present invention includes two novel aspects: 1) While the vast majority of COCs are petroleum-based paraffinic oils or esterified seed oils, this invention embodies a new oil phase, a hydrocarbon oil such exemplified by EXXON-MOBIL'S D-130, which when combined with the surfactants described herein, exhibits surprising enhancement of herbicidal activity in field tests; and 2) COC's are designed to form stable emulsions in water. The combination of cationic surfactants and phosphate esters in this invention not only form very stable emulsions in water, but, surprisingly, also form extremely stable emulsions in concentrated liquid fertilizers, including 32-0-0 fertilizer.

12 Claims, 2 Drawing Sheets

CROP OIL CONCENTRATE ADJUVANTS CONTAINING AMINE SURFACTANTS

CROSS REFERENCE TO RELATED APPLICATIONS

This application is a Divisional of U.S. patent application Ser. No. 10/591,266, pending, which is the National Phase of International Application PCT/US2005/007057 filed Mar. 3, 2005 which designated the U.S. and which claims priority to U.S. Patent Application Ser. No. 60/549,825 filed Mar. 3, 2004. The noted applications are incorporated herein by reference.

TECHNICAL FIELD

The present invention is concerned with compositions and uses of amine surfactants incorporated into crop oil concentrate (COC) adjuvants for use with various herbicides, especially glyphosate.

BACKGROUND INFORMATION

It is known in the art that surfactants are included in COCs. They function to emulsify the oil when diluted into water in the spray tank and can also be incorporated as wetters to help the spray solution spread on the target once it is applied.

BRIEF DESCRIPTION OF THE DRAWINGS

In the annexed drawings.

SUMMARY OF THE INVENTION

Figure 1:
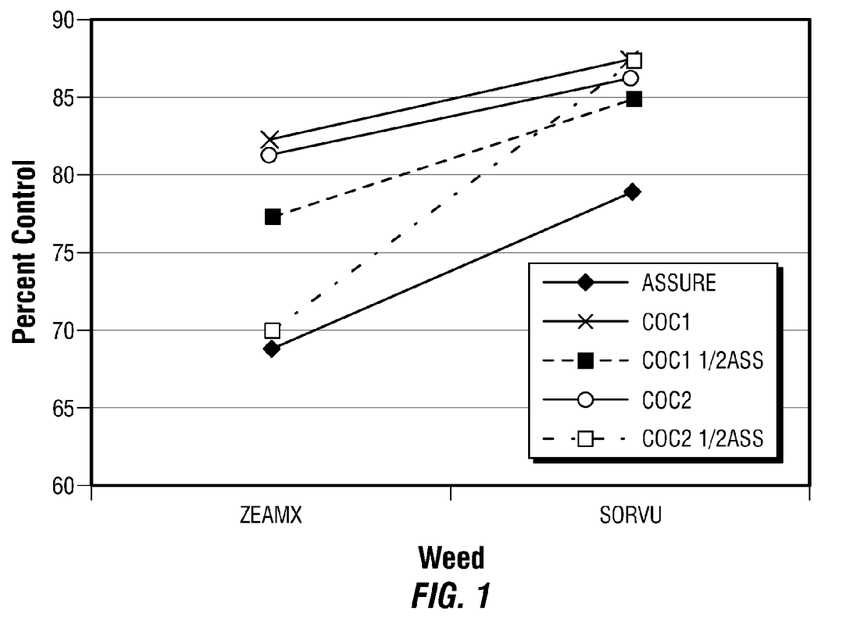
FIG. 1 shows a 10-day field trial using materials according to the present invention.
Figure 2:
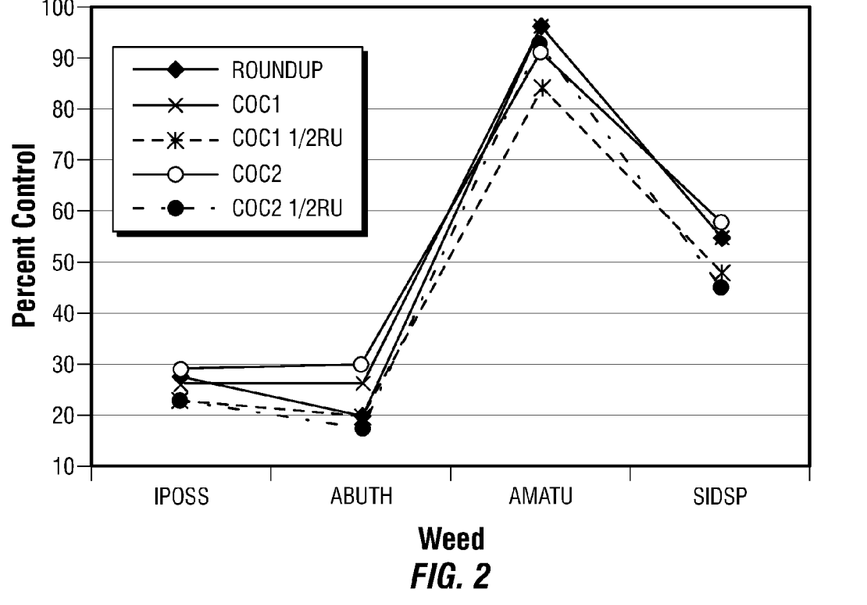
FIG. 2 shows a 10-day field trial using materials according to the present invention.
Figure 3:
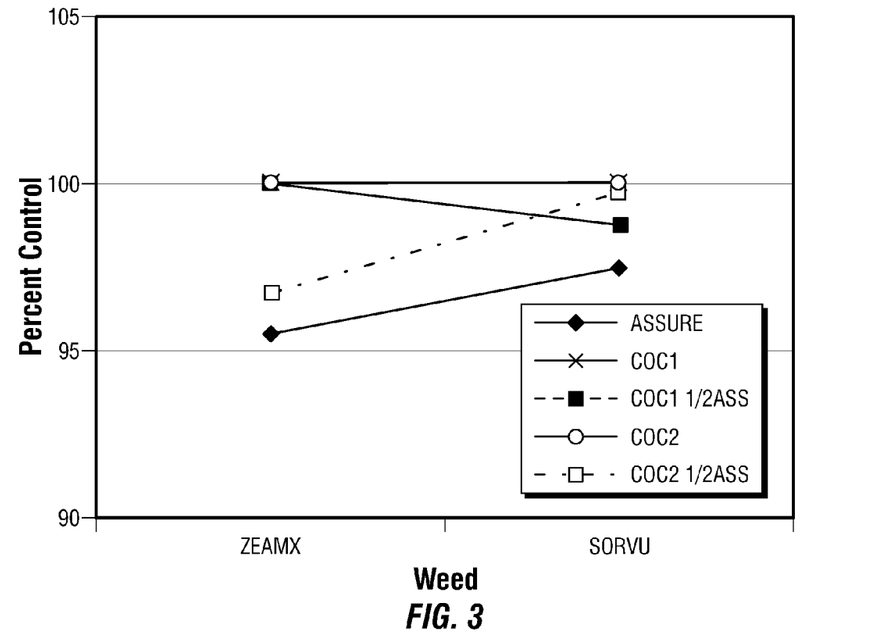
FIG. 3 shows a 21-day field trial using materials according to the present invention.
Figure 4:
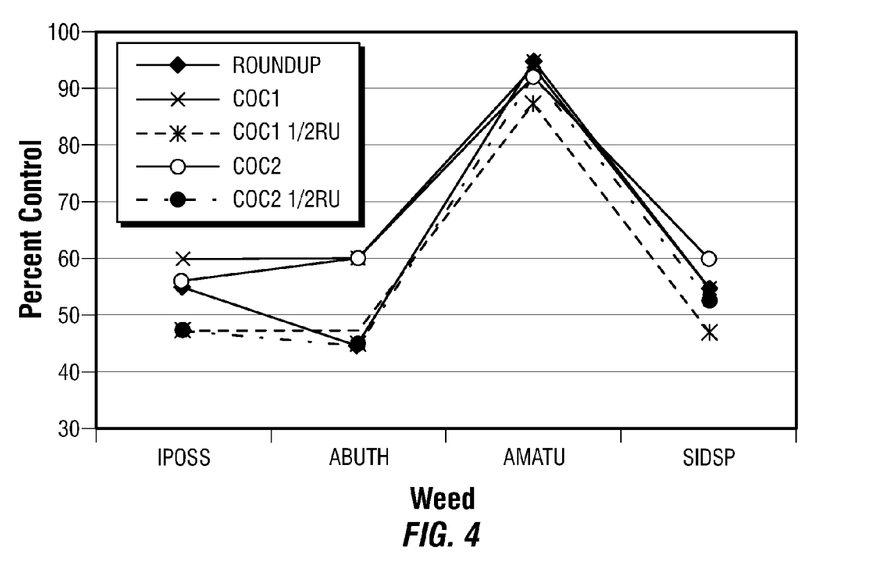
FIG. 4 shows a 21-day field trial using materials according to the present invention.

The present invention is concerned with incorporation of surfactants with amine chemistries as both emulsifier and wetter. Surfactants with amine chemistries are known to maximize the efficacy of several herbicides, especially glyphosate. By using amine chemistry surfactants in COCs that are tank mixed with pesticides that benefit from the presence of amine chemistry surfactants, the surfactants in the COCs provide dual roles in the final spray solution. They will emulsify and wet the crop oil, and they will also increase the efficacy of the active ingredient.

DETAILED DESCRIPTION

The specific surfactants used include alkyl amine ethoxylates and alkyl ether amine ethoxylates. Other amine chemistry surfactants such as polyetheramine and ethylenediamine based chemistries are useful in accordance with the present invention. The aforesaid compounds have been successfully formulated in crop oil concentrates with various paraffinic oils. In addition, formulations with EXXSOL® D130 and ester solvents EXXATE® series solvents also available from Exxon are useful. A composition according to the invention can include other surfactant chemistries, other crop oils, and optionally additional formulation components known in the art.

| Component | w/w % |
|---|---|
| Huntsman COC-1 | |
| EXXSOL® D-130 | 60.0 |
| PEL 24-3 | 28.0 |
| SURFONIC® C-2 | 4.5 |
| SURFONIC® T-10 | 5.5 |
| Water | 2.0 |
| Huntsman COC-2 | |
| EXXSOL® D-130 | 60.0 |
| PEL 24-3 | 30.0 |
| SURFONIC® PEA-25 | 8.0 |
| Water | 2.0 |

EXXSOL® D-130 is a dearomatized hydrocarbon fluid available from ExxonMobil Chemical. PE L24-3 is a phosphate ester of SURFONIC® L24-3 surfactant available from Huntsman LLC of Austin, Tex. Any phosphate esters thereof are suitable for use in the present invention. SURFONIC® C-2 is a 2-mole ethoxylate of cocoamine available from Huntsman LLC of Austin, Tex. SURFONIC® T-10 is a 10-mole ethoxylate of Tallowamine available from Huntsman LLC of Austin, Tex. SURFONIC® PEA-25 is an alkyl polyetheramine ethoxylate available from Huntsman LLC of Austin, Tex.

Unexpected results of the invention include the fact that the efficacy of active ingredient is improved by choice of adjuvant surfactant chemistry formulated into companion crop oil concentrate. Efficacy is improved past expectations from crop oil alone.

A field trial was performed with blinded sample numbers. A protocol summary of the field trial is given below:

Evaluation of Huntsman COC's with Assure® and Roundup® Original

Objective: Evaluate the performance of Huntsman crop oil concentrates compared to Agriliance HI-PER-OIL with Assure II and Roundup Original® in Roundup Ready® soybeans.

| Code | Common Name | Scientific Name |
|---|---|---|
| Target Weeds | | |
| IPOSS | Morningglory | Ipomoea spp. |
| ABUTH | Velvetleaf | Abutilon theophrasti |
| AMASS | Pigweed | Amaranthus spp. |
| SIDSP | Teaweed | Sida spinosa |
| SORVU | Shattercane | Sorghum bicolor |
| SETFA | Giant foxtail | Setaria faberi |
| ZEAMX | Volunteer RR corn | Zea mays |
| Target Crop | | |
| | Crop Common Name | |
| GLXMA | Roundup Ready® soybean | Glycine max |

Geographic Area/Environmental Considerations and General Comments: Overhead irrigation is not required, but should be supplied if drought conditions threaten loss of data.

Insure adequate broadleaf weed distribution and density by broadcasting Roundup Ready® corn seed, morning glory, velvetleaf, pigweed and prickly sida weed seeds just before the final seedbed preparation (field cultivator and/or harrow).

Plant Roundup Ready® soybeans in 30" rows. Traditional (30") row width is requested to allow maximum opportunity for emergence and aggressive growth of indigenous broadleaf weeds.

Plot size is 4 rows by 30 feet. Arrange in RCB design with 4 replications. Apply treatments in 20 gal/A spray volume.

Apply experimental treatments when most broadleaf weeds are in the 3- to 6-leaf stage. At the time of application; record the stage (number of leaves), height and density (#/sq ft or sq meter) of each broadleaf weed species that is present in sufficient density and distribution for good assessment. This data should be taken from the two center row-centers of each non-treated control plot.

Assess phytotoxicity to the crop at 2, 10, and 21 days after treatment. Include a description of the injury symptom and scale used for the assessment, i.e., necrotic leaf spots assessed as percent of leaf surface afflicted, percent crop height reduction, etc.

Assess percent (%) control of each weed species at 10 and 21 days after treatment. Crop yield is not measured. Treatments to be Evaluated:

TABLE I

| Sample No. | Name | Form | Type | Rate | Unit |
|---|---|---|---|---|---|
| 1 | Control | | | | |
| 2 | Assure II | 0.88 | EC | 4 | fl oz/A |
| 3 | Assure II | 0.88 | EC | 4 | fl oz/A |
| | HI-PER-OIL | | | 0.5 | % V/V |
| 4 | Assure II | 0.88 | EC | 2 | fl oz/A |
| | HI-PER-OIL | | | 0.5 | % V/V |
| 5 | Assure II | 0.88 | EC | 4 | fl oz/A |
| | Huntsman COC 1 | | | 0.5 | % V/V |
| 6 | Assure II | 0.88 | EC | 2 | fl oz/A |
| | Huntsman COC 1 | | | 0.5 | % V/V |
| 7 | Assure II | 0.88 | EC | 4 | fl oz/A |
| | Huntsman COC 2 | | | 0.5 | % V/V |
| 8 | Assure II | 0.88 | EC | 2 | fl oz/A |
| | Huntsman COC 2 | | | 0.5 | % V/V |
| 9 | Assure II | 0.88 | EC | 4 | fl oz/A |
| | Roundup Original | 4 | EC | 16 | fl oz/A |
| 10 | Assure II | 0.88 | EC | 4 | fl oz/A |
| | Roundup Original | 4 | EC | 16 | fl oz/A |
| | HI-PER-OIL | | | 0.5 | % V/V |
| 11 | Assure II | 0.88 | EC | 2 | fl oz/A |
| | Roundup Original | 4 | EC | 8 | fl oz/A |
| | HI-PER-OIL | | | 0.5 | % V/V |
| 12 | Assure II | 0.88 | EC | 4 | fl oz/A |
| | Roundup Original | 4 | EC | 16 | fl oz/A |
| | Huntsman COC 1 | | | 0.5 | % V/V |
| 13 | Assure II | 0.88 | EC | 2 | fl oz/A |
| | Roundup Original | 4 | EC | 8 | fl oz/A |
| | Huntsman COC 1 | | | 0.5 | % V/V |
| 14 | Assure II | 0.88 | EC | 4 | fl oz/A |
| | Roundup Original | 4 | EC | 16 | fl oz/A |
| | Huntsman COC 2 | | | 0.5 | % V/V |
| 15 | Assure II | 0.88 | EC | 2 | fl oz/A |
| | Roundup ® Original | 4 | EC | 8 | fl oz/A |
| | Huntsman COC 2 | | | 0.5 | % V/V |

Product quantities required for listed treatments and applications in one trial:

TABLE II

| Amount | Unit | Product |
|---|---|---|
| 44.0 | ml | Assure ® II 0.88 EC |
| 51.2 | ml | HI-PER-OIL |
| 51.2 | ml | Huntsman COC 1 |
| 51.2 | ml | Huntsman COC 2 |
| 88.0 | ml | Roundup Original ® 4 EC |

Calculations based on 20 gal/A spray volume, mix size=2.565 liters.

Evaluation of Huntsman COCs with Assure and Roundup Original—continued

Protocol Spray Sheet Reps: 4; Plots: 10 by 30 feet
Spray Vol: 20 gal/ac Mix Size: 2.565 liters

TABLE III

| Sample No. | Name | Form | Type | Rate | Unit | to Measure |
|---|---|---|---|---|---|---|
| 1 | Control | | | | | |
| 2 | Assure II | 0.88 | EC | 4 | fl oz/A | 4.0 ml |
| 3 | Assure II | 0.88 | EC | 4 | fl oz/A | 4.0 ml |
| | HI-PER-OIL | | | 0.5 | % V/V | 12.8 ml |
| 4 | Assure II | 0.88 | EC | 2 | fl oz/A | 2.0 ml |
| | HI-PER-OIL | | | 0.5 | % V/V | 12.8 ml |
| 5 | Assure II | 0.88 | EC | 4 | fl oz/A | 4.0 ml |
| | Huntsman COC 1 | | | 0.5 | % V/V | 12.8 ml |
| 6 | Assure II | 0.88 | EC | 2 | fl oz/A | 2.0 ml |
| | Huntsman COC 1 | | | 0.5 | % V/V | 12.8 ml |
| 7 | Assure II | 0.88 | EC | 4 | fl oz/A | 4.0 ml |
| | Huntsman COC 2 | | | 0.5 | % V/V | 12.8 ml |
| 8 | Assure II | 0.88 | EC | 2 | fl oz/A | 2.0 ml |
| | Huntsman COC 2 | | | 0.5 | % V/V | 12.8 ml |
| 9 | Assure II | 0.88 | EC | 4 | fl oz/A | 4.0 ml |
| | Roundup Original | 4 | EC | 16 | fl oz/A | 16.0 ml |
| 10 | Assure II | 0.88 | EC | 4 | fl oz/A | 4.0 ml |
| | Roundup Original | 4 | EC | 16 | fl oz/A | 16.0 ml |
| | HI-PER-OIL | | | 0.5 | % V/V | 12.8 ml |
| 11 | Assure II | 0.88 | EC | 2 | fl oz/A | 2.0 ml |
| | Roundup Original | 4 | EC | 8 | fl oz/A | 8.0 ml |
| | HI-PER-OIL | | | 0.5 | % V/V | 12.8 ml |
| 12 | Assure II | 0.88 | EC | 4 | fl oz/A | 4.0 ml |
| | Roundup Original | 4 | EC | 16 | fl oz/A | 16.0 ml |
| | Huntsman COC 1 | | | 0.5 | % V/V | 12.8 ml |
| 13 | Assure II | 0.88 | EC | 2 | fl oz/A | 2.0 ml |
| | Roundup Original | 4 | EC | 8 | fl oz/A | 8.0 ml |
| | Huntsman COC 1 | | | 0.5 | % V/V | 12.8 ml |
| 14 | Assure II | 0.88 | EC | 4 | fl oz/A | 4.0 ml |
| | Roundup Original | 4 | EC | 16 | fl oz/A | 16.0 ml |
| | Huntsman COC 2 | | | 0.5 | % V/V | 12.8 ml |
| 15 | Assure II | 0.88 | EC | 2 | fl oz/A | 2.0 ml |
| | Roundup Original | 4 | EC | 8 | fl oz/A | 8.0 ml |
| | Huntsman COC 2 | | | 0.5 | % V/V | 12.8 ml |

Assure II and Roundup Original® were the active ingredients tested.

TABLE IV

| Weed Species Studied |
|---|
| ZEAMX = Volunteer Roundup Ready ® field corn |
| SORVU = shattercane (*Sorghum bicolor*) |
| IPOSS = morningglory (*Ipomoea* spp.) |
| ABUTH = velvetleaf (*Abutilon theophrasti*) |
| AMATU = tall waterhemp (*Amaranthus tuberculatus*) |
| SIDSP = prickly sida [a.k.a. teaweed] (*Sida spinosa*) |

Results of the field trial are in the attached 10-Day and 21-Day tables:

TABLE V

10 DAY
Evaluation of Huntsman Surfactants with Assure on Roundup Ready Soybeans

| Weed Code | | | | ZEAMX | SORVU | IPOSS | ABUTH | AMATU | SIDSP |
|---|---|---|---|---|---|---|---|---|---|
| Crop Code | | | GLXMA | | | | | | |
| Rating Data Type | | | PHYGEN | CONTRO | CONTRO | CONTRO | CONTRO | CONTRO | CONTRO |
| Rating Unit | | | % | % | % | % | % | % | % |
| Weed Stage | | | | 7 leaf | 6 leaf | 9 leaf | 9 leaf | 9 leaf | 9 leaf |
| Trt-Eval Interval | | | 10 DA-A | 10 DA-A | 10 DA-A | 10 DA-A | 10 DA-A | 10 DA-A | 10 DA-A |
| Treatment | Rate | Plot | | | | | | | |
| Control | | 101 | 0 | 0 | 0 | 0 | 0 | 0 | 0 |
| | | 206 | 0 | 0 | 0 | 0 | 0 | 0 | 0 |
| | | 310 | 0 | 0 | 0 | 0 | 0 | 0 | 0 |
| | | 404 | 0 | 0 | 0 | 0 | 0 | 0 | 0 |
| | | avg | 0 | 0 | 0 | 0 | 0 | 0 | 0 |
| Assure II | 4 | 102 | 0 | 60 | 70 | 0 | 0 | 0 | 0 |
| | | 204 | 0 | 70 | 85 | 0 | 0 | 0 | 0 |
| | | 312 | 0 | 70 | 80 | 0 | 0 | 0 | 0 |
| | | 408 | 0 | 75 | 80 | 0 | 0 | 0 | 0 |
| | | avg | 0 | 69 | 79 | 0 | 0 | 0 | 0 |
| Assure II | 4 | 105 | 0 | 80 | 90 | 0 | 0 | 0 | 0 |
| Huntsman COC-1 | 0.5 | 208 | 0 | 85 | 85 | 0 | 0 | 0 | 0 |
| | | 313 | 0 | 85 | 90 | 0 | 0 | 0 | 0 |
| | | 412 | 0 | 80 | 85 | 0 | 0 | 0 | 0 |
| | | avg | 0 | 83 | 88 | 0 | 0 | 0 | 0 |
| Assure II | 2 | 106 | 0 | 60 | 80 | 0 | 0 | 0 | 0 |
| Huntsman COC-1 | 0.5 | 207 | 0 | 80 | 80 | 0 | 0 | 0 | 0 |
| | | 309 | 0 | 85 | 90 | 0 | 0 | 0 | 0 |
| | | 414 | 0 | 85 | 90 | 0 | 0 | 0 | 0 |
| | | avg | 0 | 78 | 85 | 0 | 0 | 0 | 0 |
| Assure II | 4 | 107 | 0 | 80 | 90 | 0 | 0 | 0 | 0 |
| Huntsman COC-2 | 0.5 | 211 | 0 | 80 | 85 | 0 | 0 | 0 | 0 |
| | | 308 | 0 | 85 | 85 | 0 | 0 | 0 | 0 |
| | | 415 | 0 | 80 | 85 | 0 | 0 | 0 | 0 |
| | | avg | 0 | 81 | 86 | 0 | 0 | 0 | 0 |
| Assure II | 2 | 108 | 0 | 70 | 80 | 0 | 0 | 0 | 0 |
| Huntsman COC-2 | 0.5 | 212 | 0 | 80 | 90 | 0 | 0 | 0 | 0 |
| | | 305 | 0 | 70 | 90 | 0 | 0 | 0 | 0 |
| | | 401 | 0 | 60 | 90 | 0 | 0 | 0 | 0 |
| | | avg | 0 | 70 | 88 | 0 | 0 | 0 | 0 |
| Assure II | 4 | 109 | 0 | 80 | 90 | 20 | 20 | 95 | 40 |
| Roundup | 16 | 202 | 0 | 60 | 90 | 20 | 20 | 95 | 70 |
| Original ® | | | | | | | | | |
| | | 301 | 0 | 80 | 85 | 40 | 20 | 95 | 50 |
| | | 410 | 0 | 80 | 85 | 30 | 20 | 98 | 60 |
| | | avg | 0 | 75 | 88 | 28 | 20 | 96 | 55 |
| Assure II | 4 | 112 | 0 | 80 | 90 | 30 | 20 | 95 | 60 |
| Roundup | 16 | 214 | 0 | 85 | 85 | 30 | 30 | 95 | 40 |
| Original ® | 0.5 | 311 | 0 | 80 | 90 | 20 | 30 | 95 | 60 |
| Huntsman | | 406 | 0 | 75 | 90 | 25 | 25 | 95 | 60 |
| COC | | avg | 0 | 80 | 89 | 26 | 26 | 95 | 55 |
| 7945-94-1 | | | | | | | | | |
| Assure II | 2 | 113 | 0 | 80 | 85 | 20 | 20 | 95 | 60 |
| Roundup | 8 | 203 | 0 | 70 | 90 | 30 | 20 | 90 | 50 |
| Original ® | 0.5 | 304 | 0 | 80 | 80 | 20 | 20 | 70 | 50 |
| Huntsman COC-1 | | 402 | 0 | 75 | 90 | 20 | 20 | 80 | 30 |
| | | avg | 0 | 76 | 86 | 23 | 20 | 84 | 48 |
| Assure II | 4 | 114 | 0 | 85 | 90 | 20 | 20 | 95 | 50 |
| Roundup | 16 | 213 | 0 | 85 | 90 | 40 | 40 | 95 | 60 |
| Original | 0.5 | 307 | 0 | 85 | 90 | 20 | 30 | 85 | 60 |
| Huntsman COC-2 | | 405 | 0 | 80 | 90 | 35 | 30 | 90 | 60 |
| | | avg | 0 | 84 | 90 | 29 | 30 | 91 | 58 |
| Assure II | 2 | 115 | 0 | 70 | 90 | 30 | 20 | 95 | 40 |
| Roundup | 8 | 209 | 0 | 80 | 90 | 20 | 20 | 90 | 40 |
| Original | 0.5 | 315 | 0 | 60 | 90 | 20 | 10 | 90 | 50 |
| Huntsman COC-2 | | 411 | 0 | 85 | 85 | 20 | 20 | 95 | 50 |
| | | avg | 0 | 74 | 89 | 23 | 18 | 93 | 45 |

TABLE VI

21 DAY
Evaluation of Huntsman Surfactants with Assure on Roundup Ready ® Soybeans

| Weed Code | | | | ZEAMX | SORVU | IPOSS | ABUTH | AMATU | SIDSP |
|---|---|---|---|---|---|---|---|---|---|
| Crop Code | | | GLXMA | | | | | | |
| Rating Data Type | | | PHYGEN | CONTRO | CONTRO | CONTRO | CONTRO | CONTRO | CONTRO |
| Rating Unit | | | % | % | % | % | % | % | % |
| Weed Stage | | | | 8 leaf | 8 leaf | 9+ leaf | 9+ leaf | 9+ leaf | 9+ leaf |
| Trt-Eval Interval | | | 21 DA-A | 21 DA-A | 21 DA-A | 21 DA-A | 21 DA-A | 21 DA-A | 21 DA-A |
| Treatment | Rate | Plot | | | | | | | |
| Control | | 101 | 0 | 0 | 0 | 0 | 0 | 0 | 0 |
| | | 206 | 0 | 0 | 0 | 0 | 0 | 0 | 0 |
| | | 310 | 0 | 0 | 0 | 0 | 0 | 0 | 0 |
| | | 404 | 0 | 0 | 0 | 0 | 0 | 0 | 0 |
| | | avg | 0 | 0 | 0 | 0 | 0 | 0 | 0 |
| Assure II | 4 | 102 | 0 | 90 | 95 | 0 | 0 | 0 | 0 |
| | | 204 | 0 | 100 | 100 | 0 | 0 | 0 | 0 |
| | | 312 | 0 | 92 | 100 | 0 | 0 | 0 | 0 |
| | | 408 | 0 | 100 | 95 | 0 | 0 | 0 | 0 |
| | | avg | 0 | 95.5 | 97.5 | 0 | 0 | 0 | 0 |
| Assure II | 4 | 105 | 0 | 100 | 100 | 0 | 0 | 0 | 0 |
| Huntsman | 0.5 | 208 | 0 | 100 | 100 | 0 | 0 | 0 | 0 |
| COC-1 | | 313 | 0 | 100 | 100 | 0 | 0 | 0 | 0 |
| | | 412 | 0 | 100 | 100 | 0 | 0 | 0 | 0 |
| | | avg | 0 | 100 | 100 | 0 | 0 | 0 | 0 |
| Assure II | 2 | 106 | 0 | 100 | 95 | 0 | 0 | 0 | 0 |
| Huntsman | 0.5 | 207 | 0 | 100 | 100 | 0 | 0 | 0 | 0 |
| COC-1 | | 309 | 0 | 100 | 100 | 0 | 0 | 0 | 0 |
| | | 414 | 0 | 100 | 100 | 0 | 0 | 0 | 0 |
| | | avg | 0 | 100 | 98.75 | 0 | 0 | 0 | 0 |
| Assure II | 4 | 107 | 0 | 100 | 100 | 0 | 0 | 0 | 0 |
| Huntsman | 0.5 | 211 | 0 | 100 | 100 | 0 | 0 | 0 | 0 |
| COC-2 | | 308 | 0 | 100 | 100 | 0 | 0 | 0 | 0 |
| | | 415 | 0 | 100 | 100 | 0 | 0 | 0 | 0 |
| | | avg | 0 | 100 | 100 | 0 | 0 | 0 | 0 |
| Assure II | 2 | 108 | 0 | 99 | 100 | 0 | 0 | 0 | 0 |
| Huntsman | 0.5 | 212 | 0 | 100 | 100 | 0 | 0 | 0 | 0 |
| COC-2 | | 305 | 0 | 92 | 100 | 0 | 0 | 0 | 0 |
| | | 401 | 0 | 96 | 99 | 0 | 0 | 0 | 0 |
| | | avg | 0 | 96.75 | 99.75 | 0 | 0 | 0 | 0 |
| Assure II | 4 | 109 | 0 | 100 | 100 | 50 | 50 | 95 | 60 |
| Roundup | 16 | 202 | 0 | 100 | 100 | 60 | 50 | 95 | 60 |
| Original ® | | 301 | 0 | 100 | 100 | 60 | 40 | 95 | 50 |
| | | 410 | 0 | 100 | 100 | 50 | 40 | 95 | 50 |
| | | avg | 0 | 100 | 100 | 55 | 45 | 95 | 55 |
| Assure II | 4 | 112 | 0 | 100 | 100 | 60 | 60 | 95 | 50 |
| Roundup | 16 | 214 | 0 | 100 | 100 | 60 | 60 | 92 | 50 |
| Original ® | 0.5 | 311 | 0 | 100 | 100 | 60 | 60 | 95 | 60 |
| Huntsman | | 406 | 0 | 100 | 100 | 60 | 60 | 90 | 60 |
| COC-1 | | avg | 0 | 100 | 100 | 60 | 60 | 93 | 55 |
| Assure II | 2 | 113 | 0 | 100 | 100 | 50 | 50 | 90 | 50 |
| Roundup | 8 | 203 | 0 | 100 | 100 | 50 | 40 | 90 | 50 |
| Original ® | 0.5 | 304 | 0 | 100 | 100 | 40 | 50 | 85 | 40 |
| Huntsman | | 402 | 0 | 100 | 100 | 50 | 50 | 85 | 50 |
| COC-1 | | avg | 0 | 100 | 100 | 47.5 | 47.5 | 87.5 | 47.5 |
| Assure II | 4 | 114 | 0 | 100 | 100 | 40 | 40 | 92 | 60 |
| Roundup | 16 | 213 | 0 | 100 | 100 | 60 | 60 | 95 | 60 |
| Original ® | 0.5 | 307 | 0 | 100 | 100 | 60 | 70 | 95 | 60 |
| Huntsman | | 405 | 0 | 100 | 100 | 65 | 70 | 85 | 60 |
| COC-2 | | avg | 0 | 100 | 100 | 56.25 | 60 | 91.75 | 60 |
| Assure II | 2 | 115 | 0 | 100 | 99 | 50 | 30 | 95 | 50 |
| Roundup | 8 | 209 | 0 | 100 | 100 | 40 | 60 | 90 | 50 |
| Original ® | 0.5 | 315 | 0 | 100 | 100 | 40 | 40 | 92 | 60 |
| Huntsman | | 411 | 0 | 100 | 100 | 60 | 50 | 95 | 50 |
| COC-2 | | avg | 0 | 100 | 99.75 | 47.5 | 45 | 93 | 52.5 |

Ten-Day Conclusions for Assure w/o glyphosate: Efficacy of Assure II at full rates was improved by using COCs COC1 and COC2 on both ZEAMX and SORVU. After cutting Assure rates in half, efficacy on both ZEAMX and SORVU using COC-1 was almost retained at the full rate with COC, and was significantly above full rate w/o COC. After cutting Assure rates in half, efficacy on ZEAMX using COC-2 was slightly lower than full rate with COC, but was still above full rate w/o COC. Efficacy on SORVU using COC-2 was retained at the full rate with COC, and was significantly above full rate w/o COC.

Ten-Day Conclusions for Assure with glyphosate: Data is not significantly different within individual weed species.

Twenty-one-Day Conclusions for Assure w/o glyphosate: Efficacy of Assure II at full rates was improved by using both COCs on both ZEAMX and SORVU. After cutting Assure rates in half, efficacy on both ZEAMX and SORVU using both COCs was almost retained at the full rate with COC, and was above the full rate w/o COC.

Twenty-one-Day Conclusions for Assure with glyphosate: On IPOSS, efficacy was slightly improved with COCs at full glyphosate rate, and only slightly less than full rate when glyphosate rate was cut in half. For ABUTH, efficacy was improved with COCs at full glyphosate rate, and equal to the full rate when glyphosate rate was cut in half. For AMATU, efficacies were not significantly different for glyphosate at full rate, glyphosate plus COCs at full rate, and COC-2 with glyphosate at half rate. Efficacy was only slightly reduced with COC-1 and glyphosate at half rate. For SIDSP, COC-2 improved efficacy over glyphosate at full rate, and matched efficacy of glyphosate at full rate w/o COC when glyphosate rate was cut in half. COC-1 matched full glyphosate efficacy at full glyphosate rate, but COC-1 efficacy at half glyphosate rate was slightly reduced.

Thus, the present invention provides blend compositions comprising: a) a first surfactant which comprises an alkoxylated amine; b) a second surfactant which comprises a phosphate ester; and c) and oil phase. The invention further comprises a microemulsion which comprises a blend composition as just described, in combination with water and a herbicidally-active or pesticidal ingredient.

An amine surfactant according to the present invention is one or more materials selected from the group consisting of:

a) one or more materials represented by the structure:

in which $R_1$ is any $C_8$-$C_{30}$ saturated, unsaturated, linear, or branched alkyl group and/or any $C_8$-$C_{30}$ alkyl, alkaryl (linear or branched); $R_2$ is any $C_2$-$C_6$ alkyl (linear or branched) or combinations thereof; x+y is in the range of between about 2 and 50; and Z is in the range of 0 to 10;

b) one or more materials represented by the structure:

in which $R_1$ is any $C_2$ to $C_6$ alkyl (linear or branched) group; $R_2$ is any $C_2$ to $C_6$ alkyl (linear or branched) or combinations thereof; and w+x+y+z is in the range of 4 to 50;

c) one or more materials represented by the structure:

in which $R_1$ is a $C_8$ to $C_{30}$ alkyl (saturated, unsaturated, linear or branched), and/or $C_8$ to $C_{30}$ alkyl, alkylaryl (linear or branched); $R_2$ is any $C_2$ to $C_6$ alkyl (linear or branched); and $R_3$ is any $C_1$ to $C_6$ alkyl (linear or branched) group;

d) one or more materials represented by the structure:

in which $R_1$ is a $C_8$ to $C_{30}$ alkyl (saturated, unsaturated, linear or branched), and/or $C_8$ to $C_{30}$ alkyl, alkylaryl (linear or branched); $R_2$ is any $C_2$ to $C_6$ alkyl (linear or branched); and $R_3$ is any $C_2$ to $C_6$ alkyl (linear or branched) or combinations thereof; and x+y is in the range of 2-50, including mixtures of any of the foregoing four.

A phosphate ester surfactant according to the present invention comprises one or more materials represented by the structural formula:

in which $R_1$ and $R_2$ are each independently selected from the group consisting of H, and any $C_9$ to $C_{30}$ alkyl (linear, branched, saturated, unsaturated or combinations thereof) condensed with 0 to 30 moles of one or more of $C_2$-$C_6$ alkylene oxides, and/or $C_8$-$C_{30}$ alkyl, alkaryl (alkyl is linear and/or branched) condensed with 0-30 moles of one or more of $C_2$ to $C_6$ alkylene oxides and/or combination of aforementioned alkoxylated alkyl and alkyl, alkaryl, subject to the proviso that both $R_1$ and $R_2$ are not both simultaneously H.

Agriculturally-Active Materials

As used in this specification and the appended claims, the words "agriculturally active material" means any chemical substance that: 1) when applied to a given foliage that is generally regarded as undesirable adversely affects the longevity and/or reproductive capability of such foliage; or 2) when applied to a vicinity where insects dwell adversely affects the longevity and/or reproductive capability of such insects; 3) is regarded by those skilled in the art as possessing agriculturally-beneficial properties, including insecticidal, herbicidal, fungicidal, and growth-enhancing properties. Include within this definition, without limitation, are those chemical materials such as: 2,4,5-T, Acephate, Acetamiprid, Acrinathrin, Aldicarb, Amitraz, Amitrole, Arsenic and its compounds, Bendiocarb, Benfuresate, Bensulfuron methyl, Bentazone, BHC, 2,4-D Bitertanol, Butamifos, Butylate, Cadusafos, Captafol(Difolatan), Captan, Carbaryl, Chinomethionat, Chlorfenvinphos, Chlorfluazuron, Chlorimuron ethyl, Chlormequat, Chlorobenzilate, Chlorpropham, Chlorpyrifos, Chlorthalonil, Cinmethylin, Clofentezine, Copper terephthalate trihydrate, Cyanide compounds, Cyfluthrin, Cyhalothlin, Cyhexatin, Cypermethrin, Cyproconazole, Cyromazine, Daminozide, DCIP, DDT(including DDD,DDE), Deltamethrin, Demeton, Diazinon, Dicamba, Dichlofluanid, Dichlorvos, Diclomezine, Dicofol (Kelthane), Dieldrin(including Aldrin), Diethofencarb, Difenoconazole, Difenzoquat, Diflubenzuron, Dimethipin, Dimethoate, Dimethylvinphos, Edifenphos, Endrin, EPN, EPTC, Esprocarb, Ethiofencarb, Ethofenprox, Ethoprophos, Ethoxyquin, Etobenzanide, Etrimfos, Fenarimol, Fenbutatin oxide, Fenitrothion, Fenobucarb, Fenpyroximate, Fensulfothion, Fenthion, Fenvalerate, Flucythrinate, Flufenoxuron, Fluoroimide, Flusilazole, Flusulfamide, Flutolanil, Fluvalinate, Fosetyl, Fosthiazate, Glufosinate, Glyphosate, Guthion, Halfenprox, Heptachlor (including Heptachlor epoxide), Hexaflumuron, Hexythiazox, Imazalil, Imazosulfuron, Imibenconazole, Iminoctadine, Inabenfide, Inorganic bromide, Iprodione, Isophenphos, Isoprocarb, Lead & its compounds, Lenacil, Malathion, Maleic hydrazide, MCPA (including Phenothiol), Mepanipyrim, Mephenacet, Mepronil, Methamidophos, Methiocarb, Methoprene, Methoxychlor, Metolachlor, Metribuzin, Mirex, Myclobutanil, Nitenpyram, Oxamyl, Paclobutrazol, Parathion, Parathion-methyl, Pencycuron, Pendimethalin, Permethrin, Phenthoate, Phosalone(Rubitox), Phoxim, Picloram, Pirimicarb, Pirimiphos-methyl, Pretilachlor, Prohexadione, Propamocarb, Propiconazole, Prothiofos, Pyraclofos, Pyrazoxyfen, Pyrethrins, Pyridaben, Pyridate, Pyrifenox, Pyrimidifen, Pyriproxyfen, Quinalphos, Quinclorac, Sethoxydim, Silafluofen, Tebuconazole, Tebufenozide, Tebufenpyrad, Tecloftalam, Tefluthrin, Terbufos, Thenylchlor, Thiobencarb, Thiometon, Tralomethrin, Triadimenol, Tribenuron methyl, Trichlamide, Trichlorfon, Triclofos-methyl, Tricyclazole, Triflumizole, and Vamidothion.

Agricultural Adjuvants

Adjuvants are chemical materials which are often employed as a component of an formulation containing one or more agriculturally active materials and which are designed to perform specific functions, including wetting, spreading, sticking, reducing evaporation, reducing volatilization, buffering, emulsifying, dispersing, reducing spray drift, and reducing foaming. No single adjuvant can perform all these functions, but different compatible adjuvants often can be combined to perform multiple functions simultaneously; thus, adjuvants are a diverse group of chemical materials. Within the meaning of the term "Adjuvants" is included any substance added to the spray tank to modify a pesticide's performance, the physical properties of the spray mixture, or both.

Spray application is perhaps the weakest link in the chain of events a pesticide follows through its development process. Some researchers claim that up to 70 percent of the effectiveness of a pesticide depends on the effectiveness of the spray application. Selection of a proper adjuvant may reduce or even eliminate spray application problems associated with pesticide stability, solubility, incompatibility, suspension, foaming, drift, evaporation, volatilization, degradation, adherence, penetration, surface tension, and coverage, thereby improving overall pesticide efficiency and efficacy.

Surfactant adjuvants physically alter the surface tension of a spray droplet. For a pesticide to perform its function properly, a spray droplet must be able to wet the foliage and spread out evenly over a leaf. Surfactants enlarge the area of pesticide coverage, thereby increasing the pest's exposure to the chemical. Without proper wetting and spreading, spray droplets often run off or fail to adequately cover these surfaces. Such materials enhance the absorbing, emulsifying, dispersing, spreading, sticking, wetting or penetrating properties of pesticides. Surfactants are most often used with herbicides to help a pesticide spread over and penetrate the waxy outer layer of a leaf or to penetrate through the small hairs present on a leaf surface.

While surfactant adjuvants may be anionic, cationic, or non-ionic, the non-ionic surfactants are in most common usage. The "multi-purpose" non-ionic surfactants are composed of alcohols and fatty acids, have no electrical charge and are compatible with most pesticides. Certain other surfactants may be cationic (+ charge) or anionic (− charge) and are specialty adjuvants that are used in certain situations and with certain products. Anionic surfactants are mostly used with acids or salts, and are more specialized and used as dispersants and compatibility agents. Cationic surfactants are used less frequently but one group, the ethoxylated fatty amines, sometimes are used with the herbicide glyphosate.

Silicone-based surfactants are increasing in popularity due to their superior spreading ability. Some of these surfactants are a blend of non-ionic surfactants (NIS) and silicone while others are entirely a silicone. The combination of a NIS and a silicone surfactant can increase absorption into a plant so that the time between application and rainfall can be shortened. There are generally two types of organosilicone surfactants: the polyether-silicones that are soluble in water and the alkyl-silicones that are soluble in oil. Unlike polyether-silicone types, alkyl-silicone surfactants work well with oil-based sprays, such as dormant and summer oil sprays used in insect control. Alkyl-silicone-enhanced oil sprays can maximize insecticidal activity and even allow significantly lower pesticide use rates that reduce residue levels on crops.

Sticker adjuvants increase the adhesion of solid particles to target surfaces. These adjuvants can decrease the amount of pesticide that washes off during irrigation or rain. Stickers also can reduce evaporation of the pesticide and some slow ultraviolet (UV) degradation of pesticides. Many adjuvants are formulated as spreader-stickers to make a general purpose product that includes a wetting agent and an adhesive.

Extender adjuvants function like sticker surfactants by retaining pesticides longer on the target area, slowing volatilization, and inhibiting UV degradation.

Plant penetrant surfactants have a molecular configuration that enhances penetration of some pesticides into plants. A surfactant of this type may increase penetration of a pesticide on one species of plant but not another. Systemic herbicides, auxin-type herbicides, and some translocatable fungicides can have their activity increased as a result of enhanced penetration.

Compatibility agent adjuvants are especially useful when pesticides are combined with liquid fertilizers or other pesticides, particularly when the combinations are physically or chemically incompatible, such as in cases when clumps and/or uneven distribution occurs in the spray tank. A compatibility agent may eliminate problems associated with such situations.

Buffers or pH modifier adjuvants are generally employed to prevent problems associated with alkaline hydrolysis of pesticides that are encountered when the pH of a pesticide exceeds about 7.0 by stabilizing the pH at a relatively constant level. Extreme pH levels in the spray mixture can cause some pesticides to break down prematurely. This is particularly true for the organophosphate insecticides but some herbicides can break down into inactive compounds in a matter of hours or minutes in alkaline situations (pH>7). For example, the insecticide Cygon (dimethoate) loses 50 percent of its pest control power in just 48 minutes when mixed in water of pH 9. At a pH of 6, however, it takes 12 hours for degradation to progress to that extent. On the other hand, sulfonyl urea (SU) herbicides tend to break down more rapidly where the pH is below 7. At low pHs, the herbicide 2,4-D is an uncharged molecule. At higher pH, 2,4-D tends to become more anionic or negatively charged which can affect its movement in the environment. Leaf coatings often have a high pH that can contribute to poor performance with certain herbicides. The use of a buffering or acidifying adjuvant can stabilize or lower the pH of a spray solution thereby improving the stability of the pesticide being used.

Mineral control adjuvants are used to mask the problems associated with water hardness minerals in spray water which can diminish the effectiveness of many pesticides. Mineral ions such as calcium, magnesium, salts and carbonates are commonly found in hard water. These ions can bind with the active ingredients of some pesticides, especially the salt-formulation herbicides such as Roundup™ (glyphosate), Poast™ (sethoxydim), Pursuit™ (imazethapyr), and Liberty™ (glufosinate) resulting in poor weed control. The use of water-conditioning adjuvants gives hard water minerals something to bind with other than the herbicide. In addition, some ammonium sulfate-based adjuvants can be used to offset hard water problems.

Drift retardant adjuvants improve on-target placement of pesticide spray by increasing the average droplet size, since drift is a function of droplet size with drops with diameters of 100 microns or less tending to drift away from targeted areas.

Defoaming agent adjuvants are used to control the foam or frothy head often present in some spray tanks that results from the surfactant used and the type of spray tank agitation system can often can be reduced or eliminated by adding a small amount of foam inhibitor.

Thickener adjuvants increase the viscosity of spray mixtures which afford control over drift or slow evaporation after the spray has been deposited on the target area.

Oil-based adjuvants have been gaining in popularity especially for the control of grassy weeds. There are three types of oil-based adjuvants: crop oils, crop oil concentrates (COC) and the vegetable oils. Crop Oil adjuvants are derivative of paraffin-based petroleum oil. Crop oils are generally 95-98% oil with 1 to 2% surfactant/emulsifier. Crop oils promote the penetration of a pesticide spray either through a waxy plant cuticle or through the tough chitinous shell of insects. Crop oils may also be important in helping solubilize less water-soluble herbicides such as Poast™ (sethoxydim), Fusilade™ (fluaziprop-butyl) and atrazine. Traditional crop oils are more commonly used in insect and disease control than with herbicides. Crop oil concentrates (COC) are a blend of crop oils (80-85%) and the non-ionic surfactants (15-20%). The purpose of the non-ionic surfactant in this mixture is to emulsify the oil in the spray solution and lower the surface tension of the overall spray solution. Vegetable oils work best when their lipophilic characteristics are enhanced, and one common method of achieving this is by esterification of common seed oils such as rapeseed, soybean, and cotton. The methylated seed oils (MSO) are comparable in performance to the crop oil concentrates, in that they increase penetration of the pesticide. In addition, silicone-based MSOs are also available that take advantage of the spreading ability of the silicones and the penetrating characteristics of the MSOs.

The special purpose or utility adjuvants are used to offset or correct certain conditions associated with mixing and application such as impurities in the spray solution, extreme pH levels, drift, and compatibility problems between pesticides and liquid fertilizers. These adjuvants include acidifiers, buffering agents, water conditioners, anti-foaming agents, compatibility agents, and drift control agents.

Fertilizer-based adjuvants, particularly nitrogen-based liquid fertilizers, have been frequently added to spray solutions to increase herbicide activity. Research has shown that the addition of ammonium sulfate to spray mixtures enhances herbicidal activity on a number of hard-to-kill broadleaf weeds. Fertilizers containing ammonium nitrogen have increased the effectiveness of the certain polar, weak acid herbicides such as Accent™ (nicosulfuron), Banvel™ (dicamba), Blazer™ (acifluorfen-sodium), Roundup™ (glyphosate), Basagran™ (bentazon), Poast™ (sethoxydim), Pursuit™ (imazethapyr), and 2,4-D amine. Early fertilizer-based adjuvants consisted of dry (spray-grade) ammonium sulfate (AMS) at 17 lbs per 100 gallons of spray volume (2%). Studies of these adjuvants has shown that Roundup™ uptake was most pronounced when spray water contained relatively large quantities of certain hard water ions, such as calcium, sodium, and magnesium. It is thought that the ions in the fertilizer tied up the hard water ions thereby enhancing herbicidal action.

Consideration must be given to the fact that although this invention has been described and disclosed in relation to certain preferred embodiments, obvious equivalent modifications and alterations thereof will become apparent to one of ordinary skill in this art upon reading and understanding this specification and the claims appended hereto. The present disclosure includes the subject matter defined by any combination of any one of the various claims appended hereto with any one or more of the remaining claims, including the incorporation of the features and/or limitations of any dependent claim, singly or in combination with features and/or limitations of any one or more of the other dependent claims, with features and/or limitations of any one or more of the independent claims, with the remaining dependent claims in their original text being read and applied to any independent claim so modified. This also includes combination of the features and/or limitations of one or more of the independent claims with the features and/or limitations of another independent claim to arrive at a modified independent claim, with the remaining dependent claims in their original text being read and applied to any independent claim so modified. Accordingly, the presently disclosed invention is intended to cover all such modifications and alterations, and is limited only by the scope of the claims which follow, in view of the foregoing and other contents of this specification.

What is claimed is:

1. A microemulsion comprising:
    (a) a crop oil concentrate (COC) comprising:
        from 8 w/w % to 10 w/w % of one or more alkoxylated amine surfactant components;
        from 28 w/w % to 30 w/w % of a phosphate ester component; and
        60 w/w % of a dearomatized hydrocarbon oil component;
    (b) water; and
    (c) at least one agriculturally-active material.

2. The microemulsion of claim 1, wherein the surfactant is an alkyl amine alkoxylate.

3. The microemulsion of claim 2, wherein the surfactant is a tallow amine ethoxylate.

4. The microemulsion of claim 1, wherein the surfactant is a polyetheramine alkoxylate.

5. The microemulsion of claim 1, wherein the surfactant is an alkyl diamine alkoxylate.

6. The microemulsion of claim 1, wherein the alkoxylated amine surfactant component has a w/w % of 10 %.

7. The microemulsion of claim 6, wherein the phosphate ester surfactant component has a w/w % of 30 %.

8. A microemulsion consisting of:
    (a) a crop oil concentrate (COC) consisting of:
        from 8 w/w % to 10 w/w % of one or more alkoxylated amine surfactant components;
        from 28 w/w % to 30 w/w % of a phosphate ester component; and 60 w/w % of a dearomatized hydrocarbon oil component, (b) water; and (c) at least one agriculturally-active material.

9. The microemulsion of claim 8, wherein the alkoxylated amine surfactant component has a w/w % of 10 %.

10. The microemulsion of claim 9, wherein the phosphate ester surfactant component has a w/w % of 30 %.

11. A method of controlling weeds, comprising:
diluting a composition into a spray tank with one or more pesticides, wherein the composition comprises:
a crop oil concentrate (COC) comprising:
   from 8 w/w % to 10 w/w % of one or more alkoxylated amine surfactant components;
   from 28 w/w % to 30 w/w % of a phosphate ester component; and
   60 w/w % of a dearomatized hydrocarbon oil component, and then applying the composition to a plant.

12. The method of claim 11, wherein the COC comprises:
10 w/w % of the one or more alkoxylated amine surfactants; and
from 28 w/w % to 30 w/w % of the phosphate ester surfactant.

* * * * *